(12) United States Patent
Torp et al.

(10) Patent No.: US 7,077,807 B2
(45) Date of Patent: Jul. 18, 2006

(54) METHOD AND APPARATUS FOR PROVIDING REAL-TIME CALCULATION AND DISPLAY OF TISSUE DEFORMATION IN ULTRASOUND IMAGING

(75) Inventors: Hans Torp, Trondheim (NO); Bjorn Olstad, Stathelle (NO); Andreas Heimdal, Trondheim (NO); Steinar Bjaerum, Trondheim (NO)

(73) Assignee: G.E. Vingmed Ultrasound AS (NO)

( * ) Notice: Subject to any disclaimer, the term of this patent is extended or adjusted under 35 U.S.C. 154(b) by 253 days.

(21) Appl. No.: 10/705,190

(22) Filed: Nov. 10, 2003

(65) Prior Publication Data
US 2004/0111027 A1 Jun. 10, 2004

Related U.S. Application Data

(62) Division of application No. 10/054,033, filed on Jan. 22, 2002, now Pat. No. 6,676,599, which is a division of application No. 09/432,061, filed on Nov. 2, 1999, now Pat. No. 6,352,507.

(60) Provisional application No. 60/150,265, filed on Aug. 23, 1999.

(51) Int. Cl.
*A61B 8/00* (2006.01)
(52) U.S. Cl. .................................................. 600/438
(58) Field of Classification Search ............... 600/438, 600/443, 440, 454–456
See application file for complete search history.

(56) References Cited

U.S. PATENT DOCUMENTS

| 4,534,357 A | 8/1985 | Powers |
| 4,780,837 A | 10/1988 | Namekawa |
| 5,046,500 A | 9/1991 | Fehr |
| 5,083,566 A | 1/1992 | Baba |
| 5,109,856 A | 5/1992 | Bonnefous et al. |
| 5,183,047 A | 2/1993 | Burckhardt |
| 5,241,473 A | 8/1993 | Ishihara et al. |
| 5,457,754 A | 10/1995 | Han et al. |
| 5,462,058 A | 10/1995 | Yamada et al. |
| 5,474,070 A | 12/1995 | Ophir et al. |
| 5,501,223 A | 3/1996 | Washburn et al. |
| 5,524,636 A | 6/1996 | Sarvazyan et al. |

(Continued)

FOREIGN PATENT DOCUMENTS

EP 0509 760 10/1992

(Continued)

OTHER PUBLICATIONS

Brands P J et al,. "A noninvasive method to estimate pulse wave velocity in arteries locally by means of ultrasound," *Ultrasound In Medicine and Biology*, New York, NY, US 24(9):1325-1335 (Dec. 1998).

(Continued)

*Primary Examiner*—Francis J. Jaworski
(74) *Attorney, Agent, or Firm*—McAndrews, Held & Malloy, Ltd.; Peter J. Vogel; Michael A. Dellapenna

(57) ABSTRACT

An ultrasound system and method for calculation and display of tissue deformation parameters are disclosed. A method to estimate a strain rate in any direction, not necessarily along the ultrasound beam, based on tissue velocity data from a small region of interest around a sample volume is disclosed. Quantitative tissue deformation parameters, such as tissue velocity, tissue velocity integrals, strain rate and/or strain, may be presented as functions of time and/or spatial position for applications such as stress echo. For example, strain rate or strain values for three different stress levels may be plotted together with respect to time over a cardiac cycle.

15 Claims, 11 Drawing Sheets

U.S. PATENT DOCUMENTS

| | | | |
|---|---|---|---|
| 5,615,680 | A | 4/1997 | Sano |
| 5,673,700 | A * | 10/1997 | Yamazaki et al. .......... 600/455 |
| 5,785,654 | A | 7/1998 | Iinuma et al. |
| 5,800,356 | A | 9/1998 | Criton et al. |
| 5,840,028 | A | 11/1998 | Chubachi et al. |
| 5,876,341 | A | 3/1999 | Wang et al. |
| 6,030,344 | A * | 2/2000 | Guracar et al. ............. 600/447 |
| 6,099,471 | A | 8/2000 | Torp et al. |
| 6,352,507 | B1 | 3/2002 | Torp et al. |

FOREIGN PATENT DOCUMENTS

| | | |
|---|---|---|
| EP | 0931 508 | 7/1999 |
| WO | WO 94/23652 | 10/1994 |
| WO | WO 99/17660 | 4/1999 |

OTHER PUBLICATIONS

Brodin L-A et al., "New functional imaging options with echocardiography based on myocardial velocity curves," *Computers in Cardiology* 1998 Cleveland, OH, USA Sep. 13-16, 1998, New York, NY, USA, IEEE, US p. 253-256.

Brodin L-A et. al., "Echocardiographic Functional Images Based on Tissue Velocity Information," Herz, Urban Und Vogel, Muenchen, De. 23(8):491-498 (Dec. 8, 1998).

Flachskampf Frank, et al., "Stress-Echokardiograpie, Versuch einer Standortbestimmung" 94(9):A-523-A-528 (Feb. 28, 1997).

Heimdal A. et al., "Real-time strain rate imaging of the left ventricle by ultrasound," *J. Am. Soc. Echocardiography*, 11(11):1013-1019 (Nov. 1998).

Hein I.A., O'Brien D., "Current time-domain methods for assessing tissue motion by analysis from reflected ultrasound echoes—a review" *IEE Transactions on Ultrasonics and Frequency Control* 40(2):84-102 (Mar. 1993).

Lee S H et al., "Temporal analysis of regional synthetic M-mode to identify abnormal stress echocardiographic studies," *Computers in Cardiology* 1998 Cleveland, OH, USA Sep. 13-16, 1998, New York, NY USA, IEEE, US, pp. 241-244.

Nitzpon H J et al., "A New Pulsed Wave Doppler Ultrasound System to Measure Blood Velocities Beyond the Nyquist Limit," *IEEE Transactions on Ultrasonics, Ferroelectrics and Frequency Control*, IEEE Inc. New York, NY US 42(2):1265-279 (Mar. 1, 1995).

Nixdorf Uwe, et al., "Klinischer Stellenwert der Stressechokardiographie," *Deutsches Arzteblatt*, 94(25):A1723-A1728 (Jun. 20, 1997).

Pesavento A et al., "Time-efficient and exact algorithms for adaptive temporal stretching and 2D-correlation for elastographic imaging using phase information," Ultrasonics Symposium 1998. Proceedings., 1998 IEEE Sendai, Japan Oct. 5-8, 1998, Piscataway, NH, USA, IEEE, US, pp. 1765-1768.

R. Albiero, A. Variola, B. Dander and C. Buonanno, "DIGITAL Stress-Echocardiography Using a Public Domain Program for the Macintosh Personal Computer," *Computers and biomedical Research*, 28:433-442 (Dec. 1995).

Shimuzu, Uematus, Nakamura, Miyatake, "Peak Negative Myocardial Velocity Gradient in Early Diastole as a Noninvasive Indicator of Left Ventricular Dialstolic Function" *Journal of the American College of Cardiography*, 32(5):1418-1425 (Nov. 1, 1998).

Stalidis G et al., "Detection and moeling of infracted myocardium regions in MRI images using a contour deformable model" *Computers in Cardiology* 1995, Vienna, Austria Sep. 10-13, 1995 New York, NY, USA, IEEE, US (Sep. 1996), pp. 17-20.

Sutherland, Kukulski, Voight, D'Hooge, "Tissue Doppler Echocardiography: Future Developments" Echocardiography 16(5):509-520 (Jul. 1999).

Tanaka N., Ohtsuki S., "Alias-free interpolation technique for pulsed Doppler signal," *Journal of the Acoustical society of Japan*, 14(4):259-265 (Jul. 1993).

Urheim S, Torp H; Edvardsen T; Olstad B; Rabben S I; Heimdal A; Angelsen B; Smiseth O A. "Myocardial strain rate imaging: Validation of a new Doppler method to quantify regional myocardial function" *Journal of the American College of Cardiology*, 33(2) Suppl. A., (Feb. 1999) p. 428A.

Heimdal et al.: "Real-time Strain Velocity Imagiing (SVI)" 1997 IEEE Ultrasonics Symposium Proceedings, vol. 2, 1997, pp. 1423-1426.

Jackson et al.: "3-D Ultrasonic Imaging of Structure and Elasticity of the Carotid Bifurcation" IEEE Ultrasonic Symposium Proceedings, vol. 2, 1995, pp. 1419-1422.

Kanai et al.: "Noninvasive Evaluation of local Myocardial Thickening and its Color-Coded Imaging" IEEE Transactions and Ultrasonics, Ferroelectrics and Frequency Control, vol. 44, No. 4, Jul. 1997, pp. 752-768.

Tsutsui et al.: "Comparative Usefulness of Myocardial Velocity Gradient in Detecting Ischemic Myocardium by a Dobutamine Challenge" J. Am. Coll. Cardiol., vol. 31, 1998, pp. 89-93.

McDicken et al.: "Colour Doppler Velocity Imaging of the Myocardium" Ultrasound in Med. & Biol., vol. 18, 1992, pp. 651-654.

Palka et al.: "Differences in Myocardial Velocity Gradient Measured Throughout the Cardiac Cycle in Patients With Hypertrophic Cardiomyopathy, Athletes and Patients With Left Ventricular Hyperthrophy Due to Hypertension" J. Am. Coll. Cardiol., vol. 30, 1997, pp. 760-768.

Nowicki, et al.: "Assessment of Wall Velocity Gradient Imaging Using a Test Phantom" Ultrasound in Medicine and Biology, vol. 22, 1996, pp. 1255-1260.

Uematsu, et al.: Myocardial Velocity Gradient as a New Indicator of Regional Left Ventricular Contraction: Detection by a Two-Dimensional Tissue Doppler Imaging Technique >> J. Am. Coll. Cardiol., 401. 26, 1995, pp. 217-223.

Fleming et al.: "Myocardial velocity gradients detected by Doppler imaging" The British Journal of Radiology, vol. 67, 1994, pp. 679-688.

Hartley et al.: "Doppler Measurement of Myocardial Thickening with a Single Epicardial Transducer" Am. J. Physiol., vol. 245, 1983, pp. H1066-H1072.

O'Donnel et al.: "Internal Displacement and Strain Imaging Using Ultrasonic SpeckleTracking," IEEE Transactions on Ultrasonics, Ferroelectrics, and Frequency Control, vol. 41, No. 3, May 1994.

* cited by examiner

METHOD AND APPARATUS FOR PROVIDING REAL-TIME CALCULATION AND DISPLAY OF TISSUE DEFORMATION IN ULTRASOUND IMAGING

RELATED APPLICATIONS

This application is a Divisional Application of U.S. patent application Ser. No. 10/054,033, filed Jan. 22, 2002, now U.S. Pat. No. 6,676,599; which is a Divisional of U.S. patent application Ser. No. 09/432,061, filed Nov. 2, 1999, issued as U.S. Pat. No. 6,352,507; which is based upon U.S. Provisional Application No. 60/150,265, filed Aug. 23, 1999.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention relates to diagnostic ultrasound systems which measure and image anatomical structures, and their movement. More particularly, the present invention relates to a signal processing method and apparatus for calculation and display of tissue deformation to be used in ultrasonic imaging systems.

Recently, within the field of ultrasound imaging, physicians have become interested in using tissue deformation properties, such as tissue strain and strain velocity for clinical measurements.

The term "strain" refers to a characteristic of material being examined. For example, the strain associated with muscle tissue corresponds to a ratio of the change in muscle tissue length during a prescribed time interval to the muscle tissue's initial length. In ultrasound imaging, the rate of change of strain (e.g., strain rate, strain velocity, etc.) may be visually presented to a physician as a colorized 2-dimensional image, where variations in color correspond to different strain velocities. It has become apparent that the viability of a segment of the muscle is related to the amount of muscle strain and temporal behavior of the strain that is performed by, or is imposed on the muscle segment. Also, it has been determined that malignant tumors may be detected based on their resistance to compression.

One application of real-time strain velocity imaging is in cardiology. The strain velocity gives a direct and quantitative measure for the ability of the myocardium to contract and relax. By imaging along the myocard from an apical view, the local strain velocity component along the long axis of the heart can be measured. Measuring the local strain velocity component gives information about the local shortening and lengthening of the heart wall. By imaging from the parasternal view, the strain velocity component perpendicular to the heart wall can be found. Finding the strain velocity component perpendicular to the heart wall gives information about the local thickening of the muscle. Wall thickening measured with M-mode or from the 2D image is a commonly used measure for muscle viability. With strain velocity imaging, a direct measure for this thickening is available. The strain velocity images can potentially add to the diagnosis of a number of cardiac disorders.

Another application of strain velocity imaging is in heart transplants. Velocity variations inside the myocardium are important for the diagnosis of rejection after heart transplantation. The strain velocity images give a direct display of these velocity variations.

Another application of strain velocity imaging is in non-invasive electrophysiology. The preferred embodiment describes techniques to image the local contraction/relaxation contributions with a high spatial and temporal resolution. Local contraction/relaxation information can be used to accurately determine the localization of, for example, where the mechanical movement in the heart chambers is activated based on a cross section just below the AV-plane. Furthermore, aberrant conduction pathways (Wolf-Parkinson-White) from the atrium to the ventricle can be localized for later ablation. Even the depth inside myocard of these paths can be better localized with this invention in order to determine if the patient should be treated with catheter techniques or surgical techniques.

Another application of strain velocity imaging is in measuring cardiac wall thickening. A well established methodology in cardiac diagnosis is to acquire a M-Mode image and to measure the wall thickening of myocardium during systole. The preferred embodiment provides techniques to take this wall thickening information and measure it in real-time with a high precision in both the spatial and temporal domain. The high diagnostic relevance of the current wall thickening measurements indicates that the imaging modality described in this invention contains highly relevant information for cardiac diagnosis To understand strain velocity or strain rate in more detail, it is assumed that an object of initial length $L_0$ may be stretched or compressed or itself lengthens or contracts to a different length L. The one-dimensional strain, defined as $$\varepsilon = \frac{L - L_0}{L_0} \quad (1)$$

represents a dimensionless description of the change. If the length L is considered to be a function of time, the temporal derivative of the strain, the strain velocity, can be found using the equation:

$$\dot{\varepsilon} = \frac{\partial \varepsilon}{\partial t} \quad (2)$$

If the velocity, v of every point in the object is known, an equivalent definition of the strain velocity is:

$$\dot{\varepsilon} = \frac{\partial v}{\partial r} \quad (3)$$

These equations also provide a useful description of the deformation of the object. In Eq. 3, r is the spatial direction of the stretching or compression. The relation between Eq. 2 and Eq. 3 can be seen if the length L is defined as $L(t)=r_2(t)-r_1(t)$, and $L_0=L(t_0)$, where $r_1$ is the distance to one end of the object, and $r_2$ is the distance to the other, and letting t→t0, and letting r1→r2. As illustrated in Eq. 3, the strain velocity is in fact the spatial gradient of the velocity. The strain velocity thus measures the rate of the deformation of the object. If the strain velocity is zero, the shape of the object is not changing. If the strain velocity is positive, the length of the object is increasing, and if the strain velocity is negative, the length of the object is decreasing. Strain velocity is also known as rate-of-deformation, stretching, strain rate or velocity strain.

Strain imaging is currently an established research area in ultrasonic imaging. The degree of deformation in imaged structure may be estimated by correlation of 2D images obtained before and after a pressure increase. One disadvantage of estimating image deformation based on correlation of images is that the instantaneous value of the strain is not calculated nor displayed in real-time. The lack of a real-time capability is an important clinical disadvantage. For example, if strain imaging could be performed in real-time, strain imaging could be applied more effectively in cardiac ultrasound or could be used as an interactive inspection modality where anomalies in tissue compressibility can be visualized in real-time according to the pressure gradients that are applied to the imaged structures.

A method of position tracking has been proposed to estimate the local myocardial strain velocity based on radio frequency (RF) M-Mode acquisitions. The position tracking method is described in H. Kanai, H. Hasegawa, N. Chubachi, Y. Koiwa, and M. Tanaka, "Noninvasive evaluation of local myocardial thickening and its color-coded imaging," *IEEE Trans. on. Ultrasonics, Ferroelectrics and Frequency Control*, vol. 44, pp. 752–768, 1997. However, the method described in the Kanai et al. article has the disadvantages of poor temporal resolution and high computational cost, which render real-time imaging difficult and costly. Furthermore, the method described in the Kanai et al. article is a manual M-mode technique, not well suited to form the basis for real-time two-dimensional strain images. Also, the strain velocity is a derivative of a velocity estimate and is therefore very noise sensitive. The fundamental velocity aliasing problem that is inherent in tissue velocity imaging makes noise difficult to overcome because aliasing prevents the pulse repetition frequency from being set at a low enough rate to allow a large observation time. If the observation time could be increased, the noise robustness of the strain velocity images could be significantly improved.

Certain of the above identified difficulties are addressed and overcome according to the teachings of U.S. patent application Ser. No. 09/167,896, filed Oct. 7, 1998 and entitled "A METHOD AND APPARATUS FOR PROVIDING REAL-TIME CALCULATION AND DISPLAY OF STRAIN IN ULTRASOUND IMAGING," which is incorporated herein by reference. However, is an object of the present invention to supplement and/or improve upon such teachings. Certain additional difficulties and shortcomings of the prior art are described below.

To achieve high frame rate in color Doppler applications, two previously known techniques are commonly used: multi line acquisition (MLA) and interleaving. These techniques make it possible to acquire more data than in a basic mode, where the scanner after one pulse is received waits the specified pulse repetition time (T) before firing the next pulse in the same direction. The time to acquire a frame of Doppler data in the basic mode is:

$$t_{D0} = N_b NT, \tag{4}$$

where N is the number of pulses in each direction and $N_b$ is the number of beams in the image. A relatively small extra delay related to the change in setup of the transmitter and beamformer is ignored to simplify the discussion.

In the MLA method, a broad beam is transmitted. When receiving the echo, the signals from all the transducer elements are processed in parallel in two or more beamformers. Each beamformer time delays the element signals differently to generate different receive beams. This way, two or more beams can be acquired during the time for one pulse-echo cycle, and the frame rate can be increased correspondingly. Using MLA, the time to acquire a frame of Doppler data is $$t_{DMLA} = \frac{N_b}{N_{MLA}} NT, \tag{5}$$

where $N_{MLA}$ is the number of beams that are processed in parallel.

In the interleaving technique, the waiting time T from one pulse to the next in the same direction is utilized to send pulses in other directions, as illustrated in FIG. 1. There is however a minimum waiting time $T_0$ where no other pulses can be fired in any direction. This is given by the time for the pulse to travel to the maximum depth and back: $T_0 > 2d/c$. The number of directions that pulses are fired during the time T is called the interleave group size, $N_{int}$. This obviously has to be an integer number, and $T = N_{int} T_0$. Using interleaving, the time to acquire a frame of Doppler data becomes:

$$t_{Dint} = \frac{N_b}{N_{int} N_{MLA}} NT. \tag{6}$$

FIG. 1 illustrates the pulse order and beam directions in the interleaving method for three different interleave group sizes $N_{int}$. The number of beams, $N_b$, equals 8 and packet size, N, equals 2 in the example of FIG. 1. For interleave pattern 100, the interleave group size, $N_{int}$, equals 8, for interleave pattern 110, $N_{int}$ equals 4 and for interleave pattern 120, $N_{int}$ equals 1.

A typical scanning procedure for a tissue Doppler application is illustrated in FIG. 2. In the example of FIG. 2, the packet size N equals 3 and the interleave group size Nint equals Nb. T is the pulse repetition time, $t_T$ and $t_D$ are the times needed to acquire a tissue frame and a Doppler frame respectively, and $t_F$ is the total acquisition time for one tissue Doppler frame. A tissue frame 130 is first captured, using high beam density. The PRF used for tissue Doppler is usually so low that only one interleave group is necessary. So N Doppler subframes 132, 134 and 136 are captured separately, usually using fewer beams than in the tissue frame. The velocity is calculated from the N subframes 132, 134 and 136, color coded and then mapped onto the tissue frame. The time to acquire a tissue Doppler frame then becomes:

$$t_F = t_T + \frac{N_b}{N_{MLA}} NT, \tag{7}$$

where $t_T$ is the time required to acquire the tissue frame. It is, thus, apparent that the maximum frame rate is limited by the above described ultrasound data acquisition schemes.

It is known that tissue velocity can be estimated using either the first or the second harmonic component of the ultrasound signal. Using the second harmonic component (octave imaging) has been reported to produce an improvement in image quality in gray scale images, and the same improvement can be expected in tissue Doppler. There is however a disadvantage in that the Nyquist limit is halved when using the second harmonic instead of the fundamental component. Using a low PRF is also preferable, since the phase amplitude of the complex signal is increased compared to the noise, resulting in a lower variance in the velocity estimate. A disadvantage of using a low PRF is that the Nyquist limit is further reduced. A reduced Nyquist limit increases the risk of aliasing, which results in the misrepresentation of high velocities.

BRIEF SUMMARY OF THE INVENTION

An ultrasound system and method for calculation and display of tissue deformation parameters are disclosed.

According to one aspect of a preferred embodiment of the present invention, an ultrasound acquisition technique that allows a high frame rate in tissue velocity imaging or strain rate imaging is disclosed. With this acquisition technique the same ultrasound pulses are used for the tissue image and the Doppler based image. A sliding window technique is used for processing.

According to another aspect of a preferred embodiment of the present invention, strain is determined by an accumulation of strain rate estimates for consecutive frames over an interval. The interval may be a triggered interval generated by, for example, an R-wave in an ECG trace. The strain calculation may be improved by moving the sample volume from which the strain rate is accumulated from frame-to-frame according to relative displacement of the tissue within the original sample volume. The relative displacement of the tissue is determined by the instantaneous tissue velocity of the sample volume.

According to another aspect of a preferred embodiment of the present invention, dr, the spatial offset used in an estimation of strain rate, is varied adaptively throughout the image. The spatial offset, dr, can be maximized to cover the entire tissue segment (e.g., heart wall width) while still keeping both of the sample volumes at each end of the offset within the tissue segment. This may be accomplished by determining whether various parameters (e.g., grayscale value, absolute power estimate, magnitude of the autocorrelation function with unity temporal lag and/or magnitude of strain correlation) of the sample volumes within in the spatial offset are above a given threshold.

According to another aspect of a preferred embodiment of the present invention, a generalized strain rate estimator that is based on a weighted sum of two-sample strain rate estimators with different spatial offsets is employed. The weights are proportional to the magnitude of the strain rate correlation estimate for each spatial offset, and thus reduce the effect of noisy, i.e. poorly correlated, samples.

According to another aspect of a preferred embodiment of the present invention, an improved signal correlation estimator that uses a spatial lag in addition to the usual temporal lag is disclosed. The spatial lag is found from the tissue velocity. The improved signal correlation estimator can be utilized both in the estimation of strain rate and tissue velocity.

According to another aspect of a preferred embodiment of the present invention, tissue velocity is estimated in a manner that reduces aliasing while maintaining spatial resolution. Three copies of a received ultrasound signal are bandpass filtered at three center frequencies. The middle of the three center frequencies is centered at the second harmonic of the ultrasound signal. A reference tissue velocity is estimated from the two signals filtered at the outside center frequencies. The reference tissue velocity is used to choose a tissue velocity from a number of tissue velocities estimated from the signal centered at the second harmonic.

According to another aspect of a preferred embodiment of the present invention, a method to estimate the strain rate in any direction, not necessarily along the ultrasound beam, based on tissue velocity data from a small region of interest around a sample volume is disclosed.

According to another aspect of a preferred embodiment of the present invention, a plurality of quantitative tissue deformation parameters, such as tissue velocity, tissue velocity integrals, strain rate and/or strain, may be presented as functions of time and/or spatial position for applications such as stress echo. For example, strain rate or strain values for three different stress levels may be plotted together with respect to time over a cardiac cycle. Parameters which are derived from strain rate or strain velocity, such as peak systolic wall thickening percentage, may be plotted with respect to various stress levels.

Other objects, features, and advantages of the present invention will be apparent from the accompanying drawings and from the detailed description that follows below.

DETAILED DESCRIPTION OF THE INVENTION

A method and apparatus are described for generating diagnostic images of tissue deformation parameters, such as strain rate, strain and tissue velocity, in real time and/or in a post-processing mode. In the following description, numerous specific details are set forth in order to provide a thorough understanding of the preferred embodiments of the present invention. It will be apparent, however, to one of ordinary skill in the art that the present invention may be practiced without these specific details.

Figure 3:
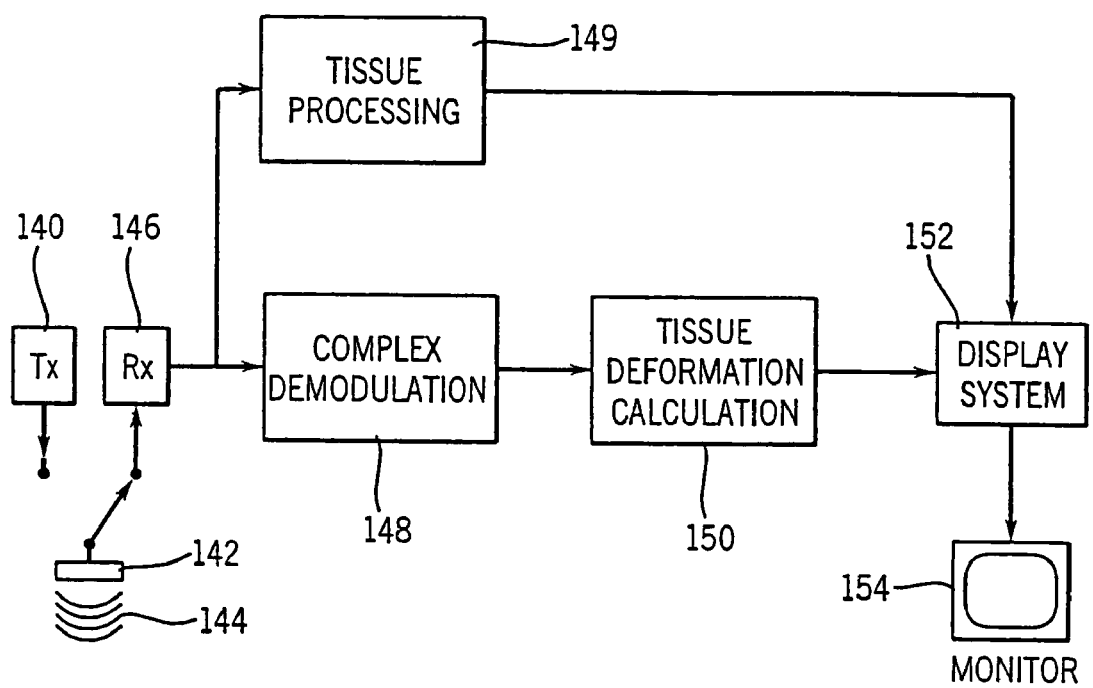
FIG. 3 illustrates an ultrasound system according to a preferred embodiment of the present invention.

A block diagram for an ultrasound imaging system according to a preferred embodiment of the present invention is shown in FIG. 3. A transmitter 140 drives an ultrasonic transducer 142 to emit a pulsed ultrasonic beam 144 into the body. The ultrasonic pulses are backscattered from structures in the body, like muscular tissue, to produce echoes which return to and are detected by the transducer 142. A receiver 146 detects the echoes. The echoes are passed from the receiver 146 to a complex demodulation stage 148 and a tissue processing stage 149. The complex demodulation stage 148 demodulates the echo signals to form I, Q data pairs representative of echo signals. The demodulated I, Q data pairs are complex Doppler signals that are passed to a tissue deformation calculation stage 150 which carries out tissue velocity, strain rate and/or strain calculations as explained below. The complex Doppler signal is associated with a sample volume defined by a range position and beam in a region of interest. A complex Doppler signal typically comprises a segment of data samples which is used to estimate the Doppler shift. The echo signals are also passed to the tissue processing stage 149, which performs processing such as B-mode processing to form a 2D or 3D image of the anatomical structure scanned.

The tissue deformation values, e.g., tissue velocity, strain rate and/or strain, output by the tissue deformation calculation stage 150 and the tissue image values output by the tissue processing stage 149 are passed to a display system 152 for display. The display system 152 includes a monitor 154.

U.S. patent application Ser. No. 09/167,896, filed Oct. 7, 1998 and entitled "A METHOD AND APPARATUS FOR PROVIDING REAL-TIME CALCULATION AND DISPLAY OF STRAIN IN ULTRASOUND IMAGING," which is incorporated herein by reference, describes a manner in which a strain rate may be estimated using the system of FIG. 3.

Figure 1:
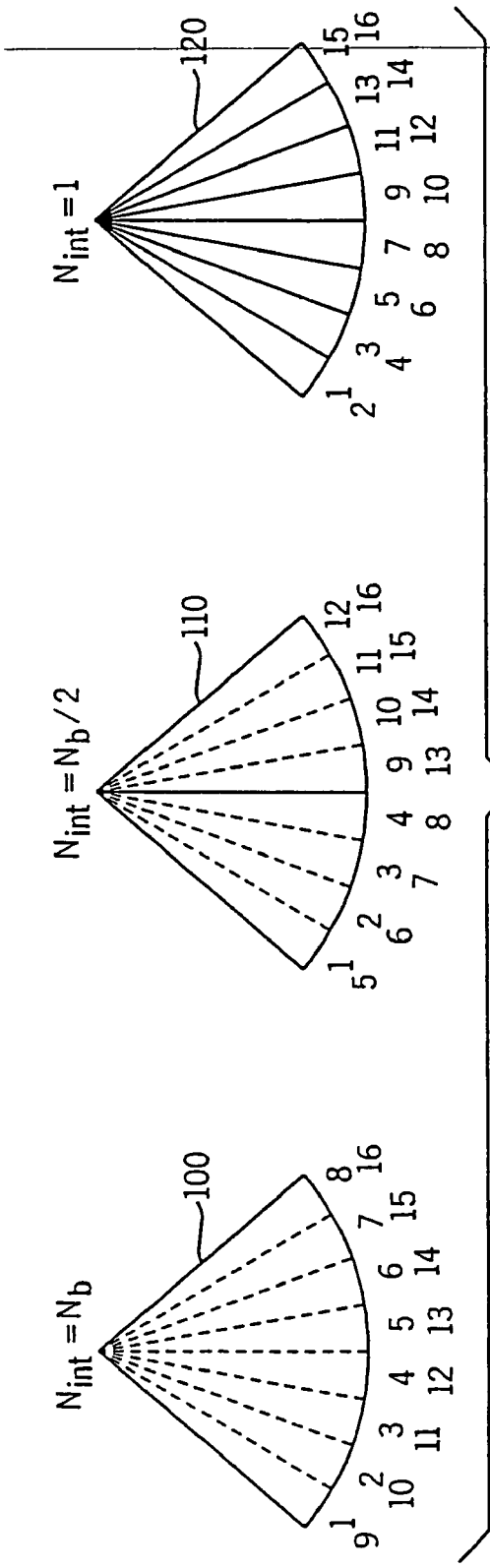
FIG. 1 illustrates the pulse order and beam direction for three different interleave group sizes.
Figure 2:
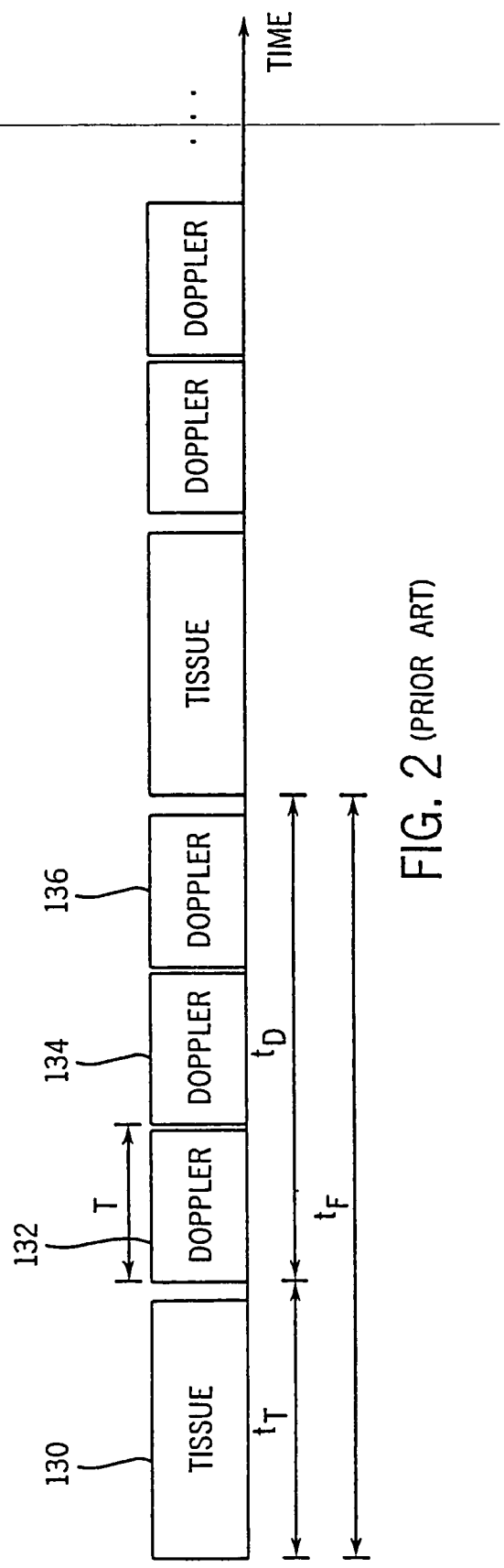
FIG. 2 illustrates a typical ultrasound acquisition procedure for a tissue Doppler application.
Figure 4:
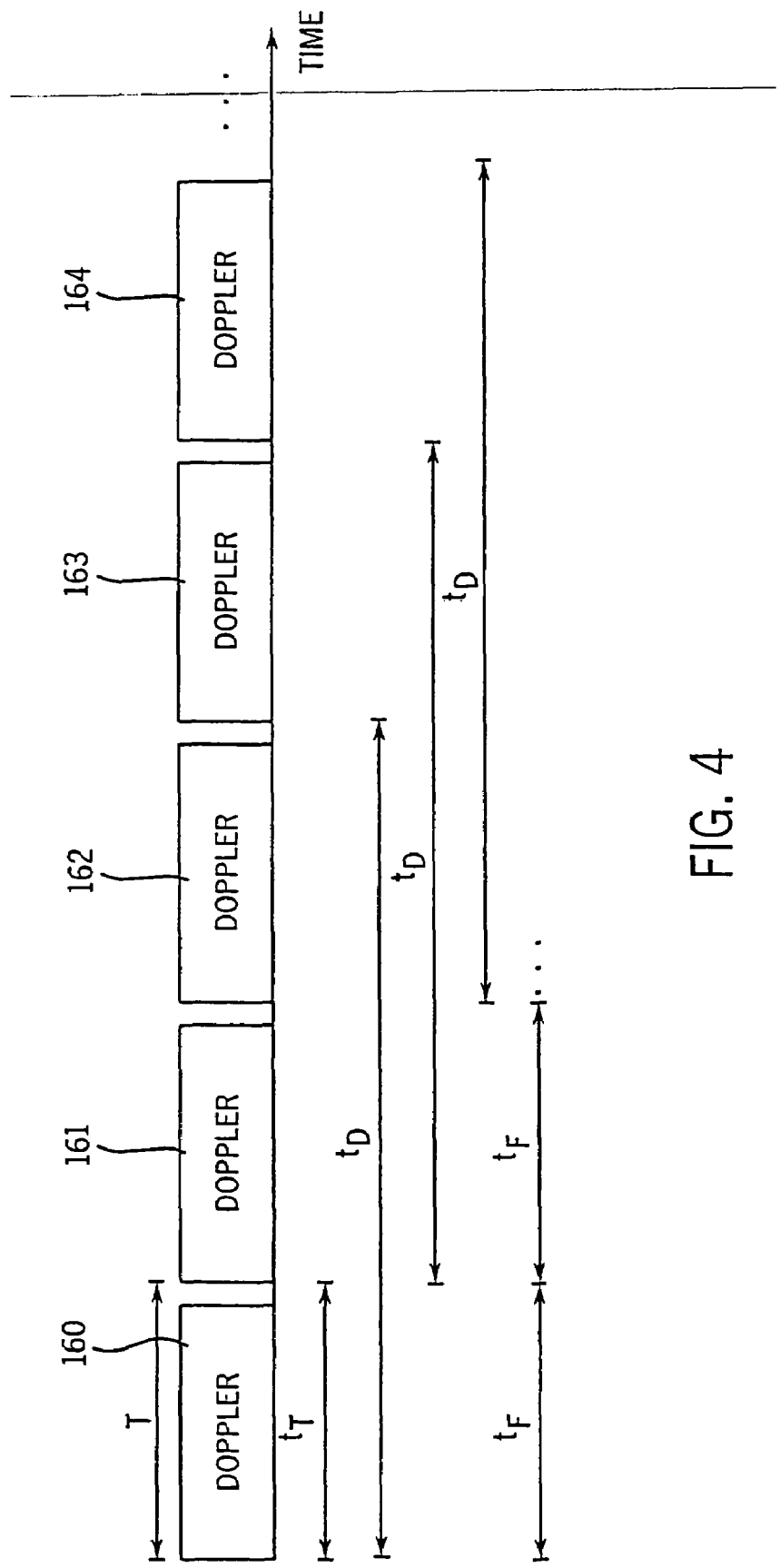
FIG. 4 illustrates an ultrasound acquisition procedure for a tissue Doppler, strain or strain rate application according to a preferred embodiment of the present invention.

For Strain Rate Imaging (SRI) and other Doppler based applications where a low pulse repetition frequency (PRF) is acceptable, a scanning procedure that allows higher frame rate may be used. Instead of collecting separate tissue frames as illustrated in FIG. 2, the number of beams in the Doppler subframes can be increased to allow tissue visualization based on only these frames. The acquisition of separate tissue frames becomes unnecessary. FIG. 4 illustrates a scanning procedure that allows a high frame rate. This scanning procedure may be used in either tissue Doppler or SRI applications. In the example of FIG. 4, the packet size N=3 and the interleave group size $N_{int}=N_b$. T is the pulse repetition time, $t_T$ and $t_D$ are the times needed to acquire a tissue frame and a Doppler frame respectively, and $t_F$ is the total acquisition time for one tissue Doppler or SRI frame. As illustrated in FIG. 4, a Doppler frame is still generated from N subframes (the subframes are numbered 160, 161, 162, 163 and 164), but a sliding window technique may be used, so the time to produce one Doppler or SRI frame will be only $$t_{FSRI} = t_T,  \quad (8)$$

assuming that the time to acquire one Doppler subframe is equal to the time to acquire one tissue frame in the conventional method. Comparing equations (7) and (8) one can see that the acquisition time for one frame is greatly reduced and, thus, allowing a higher frame rate.

One parameter that may be calculated by the tissue deformation calculation stage 150 is strain. The relation between the strain and the strain rate can be developed by way of an example. Consider a one-dimensional homogeneous object of length L(t) that has a spatially constant strain rate field s(t). The term "strain rate" is here used for the velocity gradient. The velocity field is thus given as:

$$v(t,r) = s(t)r,  \quad (9)$$

where r is the position in the object. The velocity at r=0 is set to zero for simplicity, but the same relations will apply also when v(t,0) differs from zero.

The change in length over a small time step Δt can then be estimated as $$L(t+\Delta t) - L(t) \approx \Delta t s(t) L(t).  \quad (10)$$

Letting Δt→0 we get the temporal derivative of the length:

$$\frac{dL(t)}{dt} = \lim_{\Delta t \to 0} \frac{L(t+\Delta t) - L(t)}{\Delta t} = s(t)L(t).  \quad (11)$$

The solution to this differential equation is $$L(t) = L_0 \exp\left(\int_{t_0}^{t} s(\tau) d\tau\right),  \quad (12)$$

and the strain is finally found as $$e(t) = \frac{L(t) - L_0}{L_0} \cdot 100\% = \left[\exp\left(\int_{t_0}^{t} s(\tau) d\tau\right) - 1\right] \cdot 100\%.  \quad (13)$$

The strain e(i) in a sample volume in the image can be estimated in real-time by replacing the integration in equation (13) with a cumulative sum:

$$e(i) = [\exp(C(i)) - 1] \cdot 100\%,$$

$$C(i) = C(i-1) + s(i)\Delta t.  \quad (14)$$

Here i is the frame number and Δt is the time between each frame. C(i) is the cumulative sum, and s(i) is the strain rate estimate for the given sample volume. The accumulation can also be reset at any time, for instance at a specific time trigged by an ECG-signal, by setting C(i−1) to zero for the corresponding frame number i. The calculation above can be performed for every sample volume in the image, and the visualization can be performed in the same way as for tissue velocity imageing (TVI) and SRI, only using a color map representing strain rather than tissue velocity or strain rate.

A further improvement is possible if the tissue velocity v is also available for each sample volume. In the cumulative sum for radial sample volume number $m_0$, the strain rate estimate might then be taken from a different sample volume given by the tissue velocity. First, the frame-to-frame relative displacement index is estimated as $$d = v \Delta t k_s \quad (15)$$

where v is the tissue velocity estimate in sample number $m_0$, and $k_s$ is the spatial sampling frequency. Next, the strain rate estimate from the sample volume number $$m = m_0 + d \quad (16)$$

is used in the cumulative sum, rather than $m_0$. If the tissue movement is only in the direction of the beam, this method allows the cumulative summation to track the motion of the same anatomical sample during its movement. Even if the tissue movement is in other directions, an improvement is expected.

The strain rate estimator in application Ser. No. 09/167,896 was in its simplest form described as:

$$s(r) = (v(r+dr) - v(r))/dr \quad (17)$$

where r is the radial position along an ultrasound beam, v is the tissue velocity, and dr is the spatial offset. This spatial offset can be varied adaptively throughout the image. Given an upper and lower limit on the size of dr, it can be increased as much as possible while still keeping both of the sample volumes at each end of the offset within the tissue. There are several different criteria that can be used to ensure that the offset is within the tissue. One possible criteria is that the corresponding tissue sample volumes must have a grayscale value above a given limit. Another possible criteria is that the power estimates of the sample volumes must have absolute values above a given limit. Another possible criteria is that in either of the two sample volumes, the magnitude of the autocorrelation function with unity temporal lag must be above a given limit. Another possible criteria is that the magnitude of the strain correlation (described in equation (8) in application Ser. No. 09/167,896) must be above a given limit. Any of these criteria one can be used separately, or they can be combined so that two or more criteria must be met for a positive determination that the sample volumes at the end of the offset dr are within the tissue.

The tissue deformation calculation stage 14 may calculate strain rate using a strain rate estimator that is based on several samples, and is weighted with the magnitude of a strain correlation estimate. Consider a quadrature demodulated Doppler signal x(m,n), where m is the spatial sample volume index, and n is the temporal index. The signal is assumed to have been acquired using a center frequency $f_0$, a pulse repetition time T, and a radial sampling frequency $r_s$ equal to the radial size of the point spread function. The speed of sound in the imaged object is assumed to be c. An estimator for strain rate based on M spatial and N temporal samples of the Doppler signal is:

$$s = -\frac{c}{4\pi f_0 T r_s} \frac{\sum_{m=1}^{M-1} a_m |\hat{S}(m)| \hat{\omega}_s(m)}{\sum_{m=1}^{M-1} a_m |\hat{S}(m)|}, \quad (18)$$

where $$\hat{S}(m) = \frac{1}{M-m} \sum_{k=1}^{M-m} \hat{R}^*(k) \hat{R}(k+m), \quad (19)$$

is the strain rate correlation estimate, $$\hat{\omega}_s(m) = \frac{1}{m} \angle \hat{S}(m), \quad (20)$$

is the angle of the strain rate correlation estimate, and $$a_m = m^2 \left(1 - \frac{m}{M}\right). \quad (21)$$

is a weighing factor. The signal correlation estimate $\hat{R}(m)$ is described below.

The strain rate estimator of equation (18) has certain advantages over the prior art Myocardial Velocity Gradient (MVG) technique first described in D. Fleming et al., "Myocardial velocity gradients detected by Doppler imaging" Br. J. Radiol., 67(799):679–688, 1994, and further developed by Uematsu et al., "Myocardial velocity gradient as a new indicator of regional left ventricular contraction: Detection by a two-dimensional tissue Doppler imaging technique" J. Am. Col. Cardiol., 26(1):217–23, 1995. For example, Fleming and Uematsu disclose the use of a least squares linear regression of the velocity data to obtain the velocity gradient (strain rate). Linear regression puts equal weight to all the velocity samples. The weighted strain estimator of equation (18), however, uses weights that vary with the magnitude of the strain rate correlation of equation (19) resulting in an improved strain rate estimation.

Figure 5:
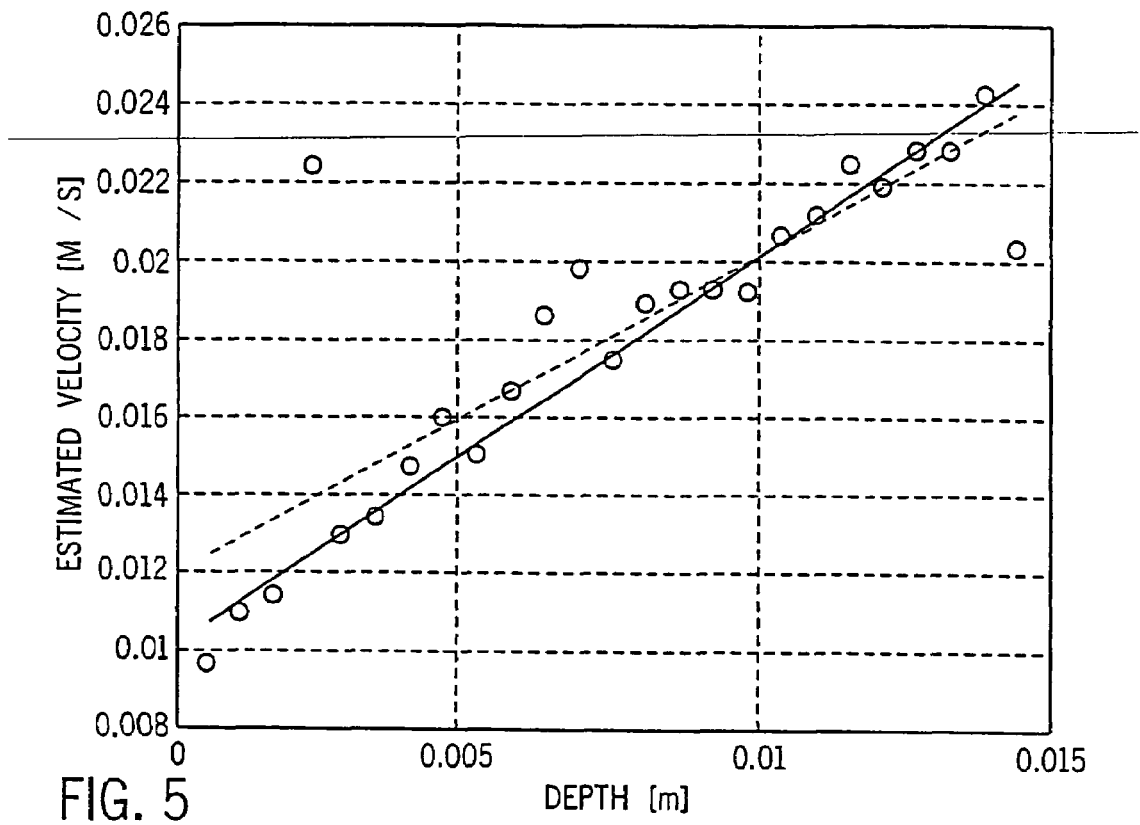
FIG. 5 illustrates a graph of the results of a computer simulated comparison of a linear regression strain rate estimator according to the prior art and a weighted strain rate estimator according to a preferred embodiment of the present invention.
Figure 6:
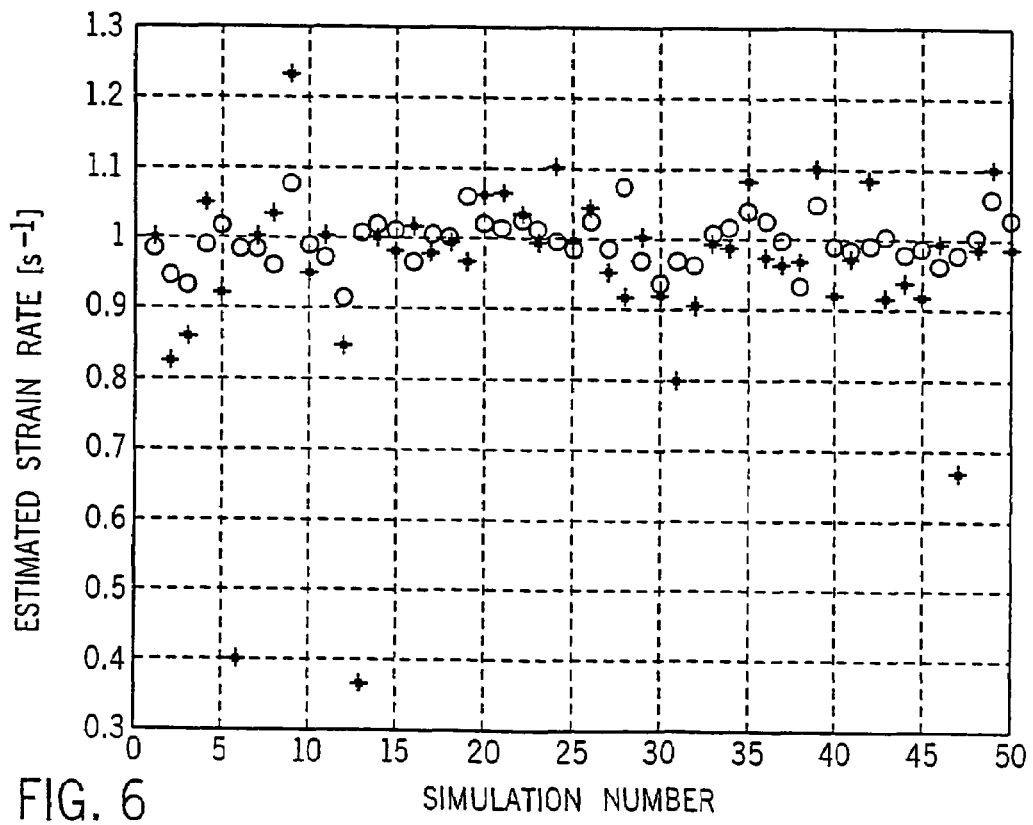
FIG. 6 illustrates a graph of the results of a computer simulated comparison of a linear regression strain rate estimator according to the prior art and a weighted strain rate estimator according to a preferred embodiment of the present invention.

FIGS. 5 and 6 illustrate a computer simulation comparison of a least squares linear regression estimator and the strain rate estimator of equation (18). FIG. 5 illustrates a linear regression fit (dashed line) and a weighted strain rate linear fit (solid line) for simulated velocity estimates (circles) at varying depths. Signals including noise were generated with a velocity gradient (strain rate) of 1.0 s$^{-1}$. A typical outcome is presented in FIG. 5. Note that the two outermost points give a large error for the linear regression line (dashed line), while the effect on the weighted strain rate estimator is much less. In FIG. 6, strain rates estimated with the linear regression method (stars) and with the weighted strain weight estimator (circles) are compared for 50 independent simulations. Once again, signals including noise were generated with a velocity gradient (strain rate) of 1.0 s$^{-1}$. The weighted strain rate estimator shows less variance than the linear regression method.

The signal correlation $\hat{R}(m)$ (used in equation (19) above) can be estimated in different ways. For example, one estimate is $$\hat{R}(m) = \sum_{n=1}^{N-1} x^*(m, n)x(m, n+1). \quad (22)$$

Spatial averaging may also be used to reduce the variance of $\hat{R}(m)$ in equation (22) and other estimators of $\hat{R}(m)$ described herein.

A more robust method to estimate the signal correlation $\hat{R}(m)$ is to introduce a spatial lag $\Delta m$, and correlate signal samples from not just the same depth m, but also from $m+\Delta m$:

$$\hat{R}(m) = \sum_{n=1}^{N-1} x^*(m, n)x(m + \Delta m, n+1). \quad (23)$$

The spatial lag $\Delta m$ preferably is chosen to maximize the magnitude of $\hat{R}(m)$. One way to chose a $\Delta m$ is through a phase root seeking technique such as described in A. Peasvento and H. Ermert, "Time-efficient and exact algorithms for adaptive temporal stretching and 2D-correlation for elastographic imaging using phase information" *Proc. of the 1998 Ultrasonic Symposium*, to be published, 1998. Alternatively, the inventors have found that the peak magnitude of $\hat{R}(m)$ is found when the spatial lag $\Delta m$ is chosen equal to the translation of the tissue from pulse to pulse:

$$\Delta m = \frac{v}{PRF}k_s, \quad (24)$$

where v is the tissue velocity, PRF is the pulse repetition frequency and $k_s$ is the spatial sampling frequency of the signal. This method requires that an un-aliased velocity estimate is available.

The tissue deformation calculation stage 150 may calculate a velocity estimate as follows. Three equal copies of the received signal are band pass filtered with three different filters. Two narrow band filters centered at $f_1$ and $f_2$, and a third wider band filter centered at $f_3$ are used, where $f_1 < f_3 < f_2$, and $f_3$ is centered around the second harmonic component of the signal. The signal correlation of each of these three signals are estimated using equation (22), resulting in the correlation estimates $\hat{R}_1(m)$, $\hat{R}_2(m)$ and $\hat{R}_3(m)$, respectively. The tissue velocity can be found from the angle of $\hat{R}_3(m)$ as:

$$\hat{v}_3 = \frac{cPRF}{4\pi f_3} \angle \hat{R}_3(m), \quad (25)$$

where c is the speed of sound. Unfortunately, the velocity estimate of equation (25) is easily aliased. A difference correlation is next found as $$\hat{R}_d(m) = \hat{R}_1^*(m)\hat{R}_2(m). \quad (26)$$

The velocity of the tissue is found from the angle of this difference correlation as $$\hat{v}_d = \frac{cPRF}{4\pi(f_2 - f_1)} \angle \hat{R}_d(m), \quad (27)$$

where c is the speed of sound. This velocity estimate is not as easily aliased since $(f_2-f_1)<f_3$. However, with equation (27) the spatial resolution is poor since narrow band signals were used in the estimation of $\hat{R}_1(m)$ and $\hat{R}_2(m)$. To this point, this two-frequency velocity estimation method is similar to a method described in Dousse et al., "Two years experience in measuring velocities beyond the Nyquist limit with Color Flow Mapper" *Proceedings of EURODOP'92*, page 219, Brighton, United Kingdom, 1992.

To regain the spatial resolution of the estimate in equation (25), the following algorithm is used: For each (possibly aliased) velocity estimate $\hat{v}_3$, several candidate velocities are found as $$\hat{v}_{3,k} = \frac{cPRF}{4\pi f_3}(\angle \hat{R}_3(m) + 2k\pi), \quad (28)$$

$$-\left\lfloor \frac{f_3 - (f_2 - f_1)}{2(f_2 - f_1)} \right\rfloor < k < \left\lfloor \frac{f_3 - (f_2 - f_1)}{2(f_2 - f_1)} \right\rfloor.$$

Next, the candidate velocity $\hat{v}_{3,k}$ that is closest to the (unaliased) difference velocity estimate $\hat{v}_d$ is chosen as the output velocity estimate. This way, the spatial resolution of the $\hat{v}_3$ estimates is kept, while avoiding the problem of aliasing.

Figure 7:
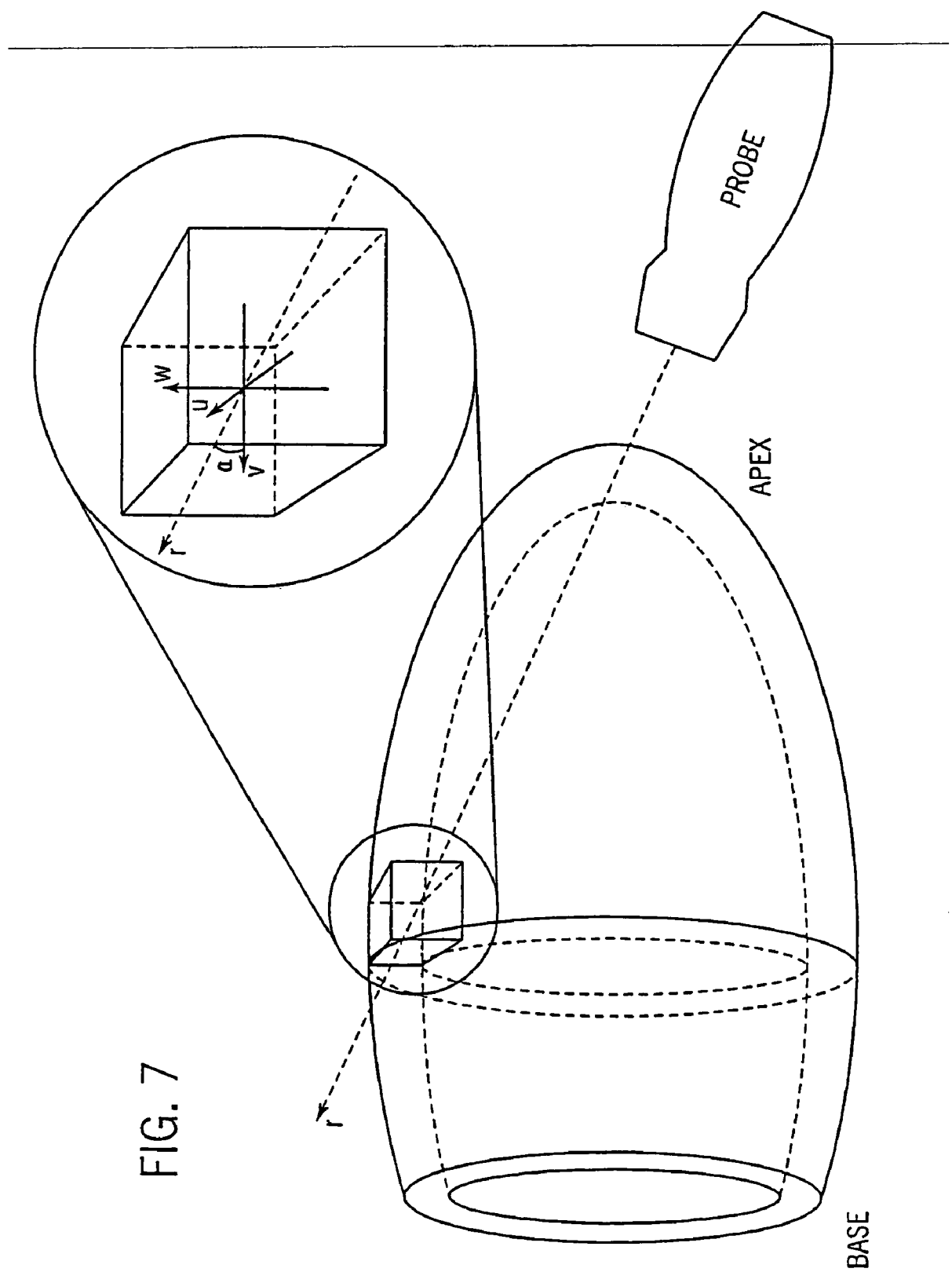
FIG. 7 illustrates the coordinates r, u, v, and w, and the insonation angle a used by a strain rate estimate angle correction technique according to a preferred embodiment of the present invention.

A method for angle correction of a strain rate estimation is described with respect to FIG. 7. Locally for each muscle segment of the left cardiac ventricle, the coordinates are defined as:
r—along the ultrasound beam, positive away from the transducer
l—lateral (beam-to-beam), positive from left to right in the ultrasound image
u—circumferential, clockwise seen from the apex
v—meridional (longitudinal), from apex to base
w—transmural, from endo- to epi-card where u, v and w will be approximately perpendicular, as shown in FIG. 7. The strain rates in these directions are termed $s_r$, $s_l$, $s_u$, $s_v$ and $s_w$, respectively. The origin (u,v,w) =(0,0,0) does not need to be defined in relation to the macroscopic ventricle geometry, and can be chosen anywhere in the imaged muscle segment.

Furthermore, $\alpha$ is defined as the angle between the v-axis and the r-axis, so that zero degrees corresponds to measuring along the muscle in the meridional direction. It is assumed that the angle $\alpha$ is in the v-w-plane (long axis or apical views), so the problem becomes two-dimensional. Note that the angle $\alpha$ is negative in FIG. 7.

Without loosing generality, it can be assumed that the point (v,w)=(0,0) is not moving. If the strain rate is spatially homogeneous over a small distance $\Delta r$ in the muscle segment, the muscle point (v,w) will then move with the velocity components:

$$v_v = v s_v \quad (29)$$

and $$v_w = w s_w. \quad (30)$$

Figure 8:
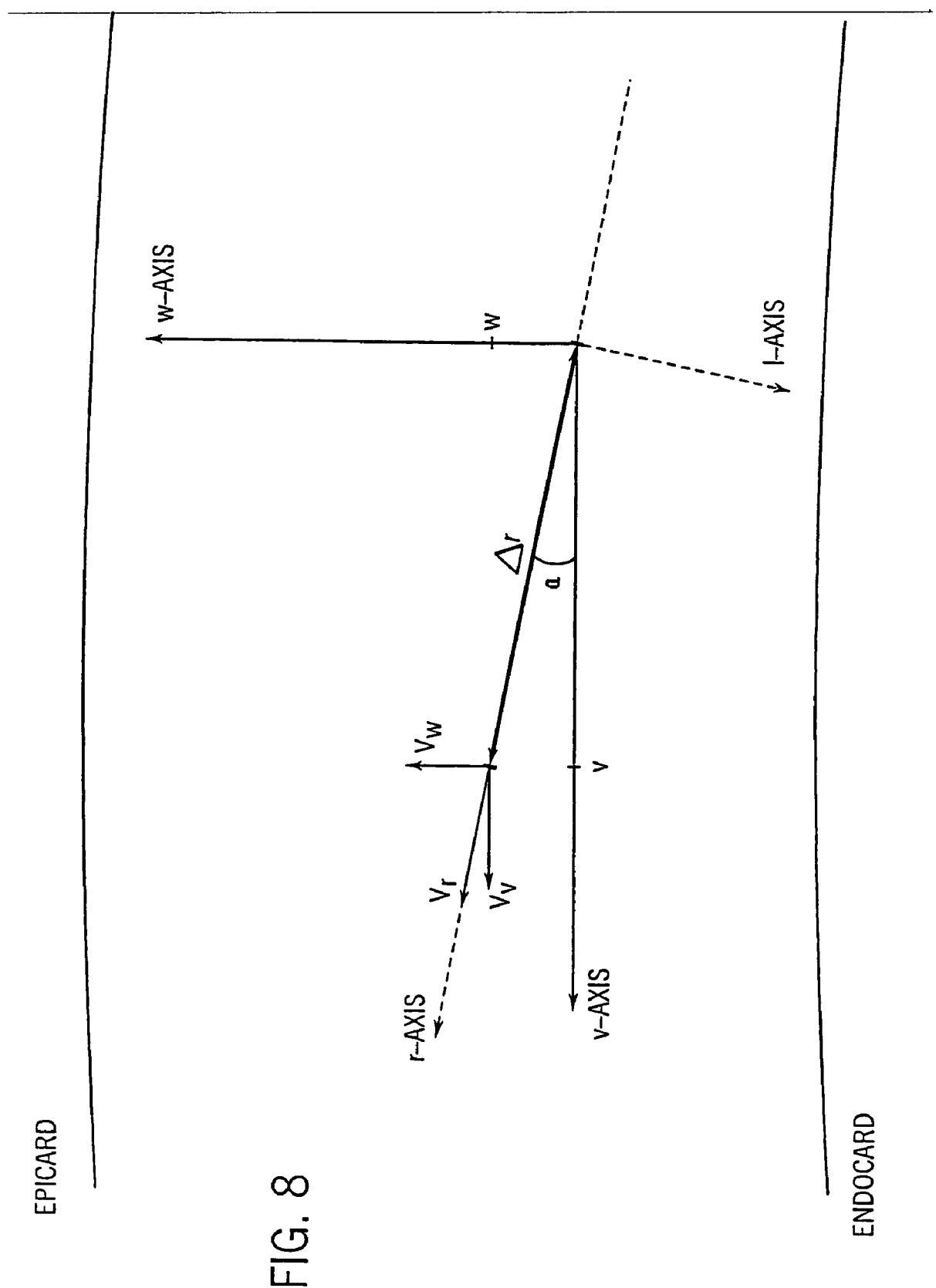
FIG. 8 illustrates the velocity components vv, vw and vr, the distance Dr and the angle a in a small muscle segment used by a strain rate estimate angle correction technique according to a preferred embodiment of the present invention.

These velocity components are shown in FIG. 8. FIG. 8 is an illustration of the velocity components $v_v$, $v_w$ and $v_r$, the distance $\Delta r$ and the angle $\alpha$ in a small muscle segment. All the parameters are drawn positive, but notice that the angle $\alpha$ is usually negative when imaging from the apex, and that $v_v$, and consequently $v_r$, normally are negative during systole. The lateral (beam-to-beam) l-axis is also included for reference. The velocity component along the ultrasound beam in position (v,w) becomes $$v_r = vs_v \cos \alpha + ws_w \sin \alpha. \quad (31)$$

Notice that the velocity $v_r$ for simplicity is defined positive away from the transducer, i.e., in positive redirection. This is opposite of the usual definition for the velocity sign in Doppler imaging.

By using velocity-information from more than one beam at a time, it is possible to calculate the strain rate in other directions than along the beam. The beams are assumed to be parallel in the region of interest. The vw-axis system is then a rotation of the lr-axis system by an angle of $(\alpha-\pi/2)$, and one can write $$v = r \cos \alpha + l \sin \alpha$$

$$w = r \sin \alpha - l \cos \alpha \quad (32)$$

Substituting these equations in equation (31) one gets $$v_r = s_v(r \cos \alpha + l \sin \alpha)\cos \alpha + s_w(r \sin \alpha - l \cos \alpha)\sin \alpha \quad (33)$$

Taking the derivatives in the two directions r and l, one gets the two equations $$\frac{\partial v_r}{\partial r} = s_v \cos^2 \alpha + s_w \sin^2 \alpha \quad (34)$$

$$\frac{\partial v_r}{\partial l} = s_v \sin\alpha\cos\alpha - s_w \sin\alpha\cos\alpha$$

Solving for $s_v$ and $s_w$ gives $$s_v = \frac{\partial v_r}{\partial r} + \frac{\partial v_r}{\partial l}\tan\alpha \quad (35)$$

$$s_w = \frac{\partial v_r}{\partial r} - \frac{\partial v_r}{\partial l}\cot\alpha$$

This means the strain rates in the anatomical directions v (meridional) and w (transmural) can be found from the radial and lateral gradients of the measured radial velocity, as long as the angle $\alpha$ is known. The image plane lr must coincide with the vw plane, which is the case for all apical views and the parasternal long axis view (PLAX). Notice that when imaging from the apex, the angle $\alpha$ will be close to zero for most of the ventricle.

The same formulas apply if one substitutes v with u, so the strain rate in the u-direction (circumferential) can also be found. The image plane lr must then coincide with the uw plane, which is the case for the short axis view (SAX).

There will be some angles where the strain rates are unavailable, though. For the u or the v directions these are the angles where $\tan \alpha$ approaches infinite values. For the w-direction these are the angles where $\cot \alpha$ approaches infinite values.

In the SAX view and using a sector scan, an approximation of $\alpha$ can automatically be found if the user defines the center of the ventricle. By assuming that the SAX cross section of the ventricle is circular, $\alpha$ at a particular location is given as $$\alpha = \frac{3\pi}{2} - \theta_b + \theta_c \quad (36)$$

where $\theta_b$ is the angle of the ultrasound beam that intersects the point ($\theta_b=0$ is defined as the center beam), and $\theta_c$ is the angle between the center ultrasound beam an imaginary beam from the center of the ventricle through the point.

A preliminary test has been performed using this two-dimensional angle correction method. A velocity data set from a healthy volunteer was obtained using tissue Doppler imaging with high beam density. The short axis view was used and the circumferential and transmural strain rate components in three phases of the cardiac cycle (mid systole, early diastolic relaxation and mid diastole) were estimated. The myocardium was segmented manually. As expected, the resulting images showed that the radial strain rate is equal to the transmural strain rate at twelve and six o'clock, and the circumferential strain rate at two and ten o'clock. Except from where the cot $\alpha$ or tan $\alpha$ approach infinity, the apparent noise in the images did not seem to be increased by this procedure.

It is also possible to perform three-dimensional angle correction. Locally for each muscle segment of the left cardiac ventricle, the coordinates are defined as:

x—azimuthal (perpendicular to the image plane)
y—lateral (beam-to-beam)
z—along the ultrasound beam
u—circumferential, clockwise seen from the apex
v—meridional (longitudinal), from apex to base
w—transmural, from endo- to epi-card where the triplets x, y, z and u, v, w locally are assumed to be perpendicular. The strain rates in these directions are termed $s_u$, $s_v$ and $s_w$, respectively. The origin (u,v,w)=(0,0,0) does not need to be defined in relation to the macroscopic ventricle geometry, and can be chosen anywhere in the imaged muscle segment.

Without loosing generality, it is assume that the point (u,v,w)=(0,0,0) is not moving. If the strain rate is spatially homogeneous over a small distance $\Delta r$ in the muscle segment, the muscle point (u,v,w) will then move with the velocity components:

$$v_u = us_u, \; v_v = vs_v, \; v_w = ws_w. \quad (37)$$

Using velocity-information from more than one beam at the time it is possible to calculate the strain rate in other directions than along the beam. The beams are assumed to be parallel in the region of interest.

Based on formulas for axis rotation it is possible to express the velocity components in the xyz-directions rather than in the uvw-directions. The velocity component in the z-direction (along the ultrasound beam), $v_z$, is the one found using Tissue Velocity Imaging. The gradients of this velocity component in each of the three spatial directions are $$v_{zr} = \frac{\partial v_z}{\partial r}, r = x, y, z \quad (38)$$

The relation to the strain rates in the uvw-directions is $$\begin{bmatrix} v_{zx} \\ v_{zy} \\ v_{zz} \end{bmatrix} = A(\alpha, \beta, \gamma) \begin{bmatrix} s_u \\ s_v \\ s_w \end{bmatrix} \quad (39)$$

where $A(\alpha,\beta,\gamma)$ is a matrix that describes the 3D axis rotation between the uvw-system and the xyz-system, and $\alpha$, $\beta$, and $\gamma$ are the rotation angles about the u-, v- and w-axis respectively. Except for certain rotation angles, this matrix can be inverted, and the strain rates can be found as:

$$\begin{bmatrix} s_u \\ s_v \\ s_w \end{bmatrix} = A^{-1}(\alpha, \beta, \gamma) \begin{bmatrix} v_{zx} \\ v_{zy} \\ v_{zz} \end{bmatrix} \quad (40)$$

Estimates for the strain rates in the uvw-directions are found by inserting velocity gradient estimators based on recorded tissue velocity data. Examples of estimators for the velocity gradients are $$\hat{v}_{zr} = \frac{v_z(r + \Delta r) - v_z(r)}{\Delta r}, r = x, y, z \quad (41)$$

where $\Delta x$, $\Delta y$, and $\Delta z$ are the sampling distances in the azimuth, lateral and radial directions in the ultrasound data respectively. Similar methods as described for 1D strain rate can also be used to estimate these velocity gradients, where the radial increment is replaced by an increment in the x- and y-directions.

A further improvement can be achieved by performing a least squares fit of the estimated strain rates to the incompressibility equation $$s_u + s_v + s_w = 0 \quad (42)$$

since muscular tissue can be considered incompressible.

In two dimensions the strain rate estimates reduce to $$s_u = v_{zz} + v_{zy} \cot \beta$$

$$s_w = v_{zz} + v_{zy} \tan \beta \quad (43)$$

for images in the uw-plane (short axis images) and $$s_v = v_{zz} + v_{zy} \cot \alpha$$

$$s_w = v_{zz} + v_{zy} \tan \alpha \quad (44)$$

for images in the vw-plane (apical images). There will be some angles where the strain rates are unavailable, though. For the u or the v directions these are the angles where tan approaches infinite values. For the w-direction these are the angles where cot approaches infinite values.

The tissue deformation calculations described herein are suited for quantitative stress echo applications. There are at least four main quantitative parameters that may be extracted, including: tissue velocity, which quantifies wall motion; tissue velocity time integrals which quantify accumulated wall motion during a time interval such as systole; strain rate (velocity gradient), which quantifies the local wall thickening at a given time instant; and strain (integrated strain rate) which quantifies local wall thickening during a time interval such as systole. These parameters are functions of both spatial position and time. From these parameters, other clinically relevant parameters may be derived. One way to present these parameters is to plot pairs of the parameters against each other (similar to pressure-volume-loops). Another useful way to present these parameters is to estimate and record (in a cineloop for example) one or more parameters from different stress levels in the stress test and then display the respective parameters from the varying stress levels simultaneously.

During a stress echo examination one of the crucial things to assess is segmental wall motion. Typically, the left ventricle is subdivided into segmental areas and a visual assessment of wall motion is done in each of these segments from the various cineloops that are acquired. The 16 segment ASE model of the left ventricle is currently the most common way to subdivide the left ventricle for scoring of stress echo exams. In a visual assessment a given segment is compared in terms of motion and wall thickening by visual comparison of similar views (2-chamber, 4-chamber, lax, sax, etc.) at different stress levels. The stress levels usually include rest, 1 or more levels of stress induced by exercise or pharmacological infusion and finally recovery. A normal reading of a segment is that both wall motion and local wall thickening increase during systole as a function of the applied stress level.

Figure 9:
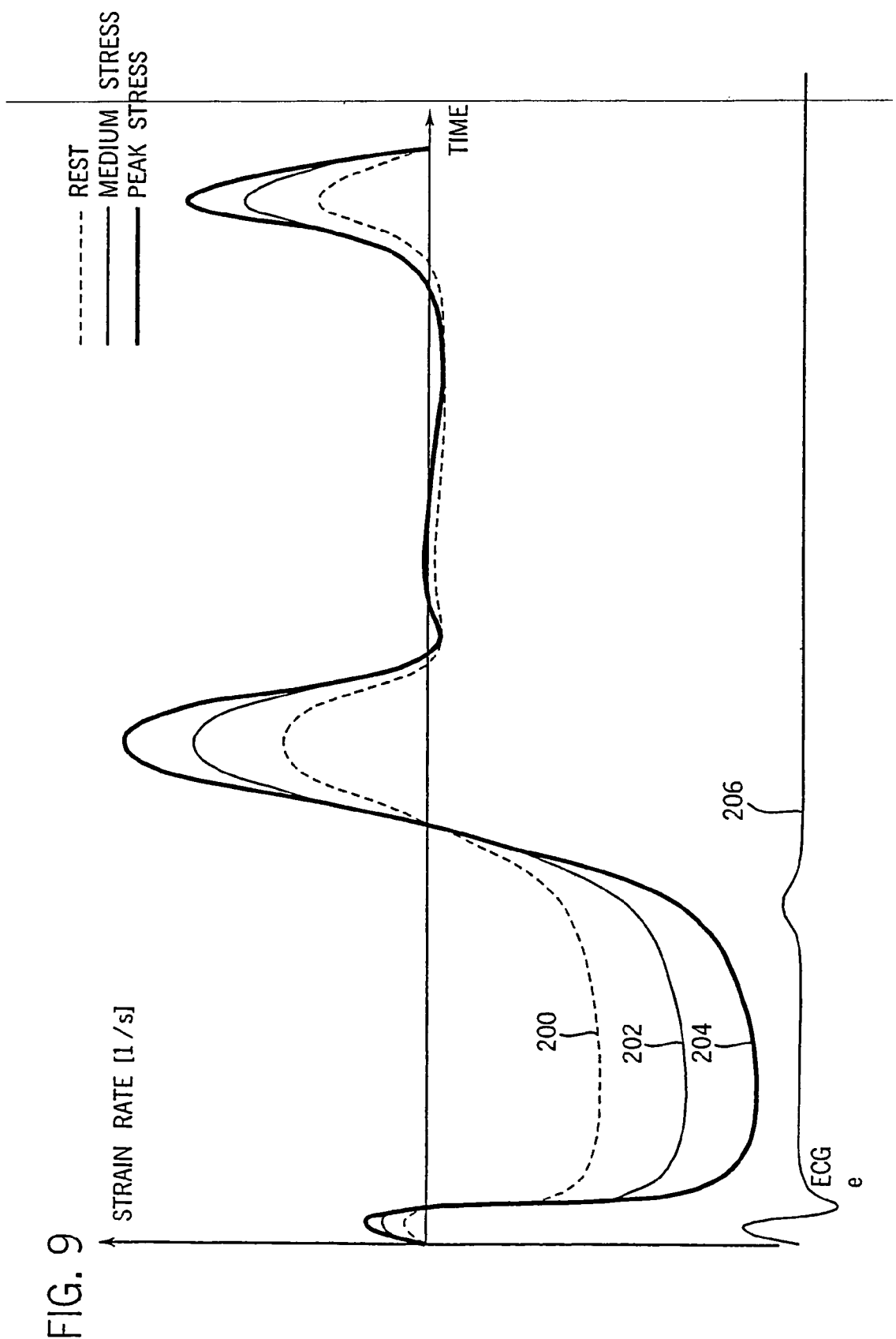
FIG. 9 illustrates a display of strain rate from multiple stress levels as a function of time for a normal case according to a preferred embodiment of the present invention.

FIG. 9 illustrates how time traces of strain rate for a given location or wall segment can be combined from multiple stress levels. Strain rates estimated during rest (line 200), medium stress (line 202) and peak stress (line 204) are plotted with respect to time. An ECG trace (line 206) is provided for reference at the bottom of the display. A difference in heart rate from the various stress levels is accounted for in this example by time scaling the different strain rate traces. This combined display contains useful clinical information about the local wall function and how the wall segment responds to an increase in stress level. The example is a typical normal reading of longitudinal shortening that can be recorded with an apical view. It should be noted that the longitudinal shortening assessed in this manner also indirectly describes wall thickening in short axis views because of conservation of mass and incompressibility of myocard. The example illustrates a normal reading where longitudinal shortening increases with the stress level.

Figure 10:
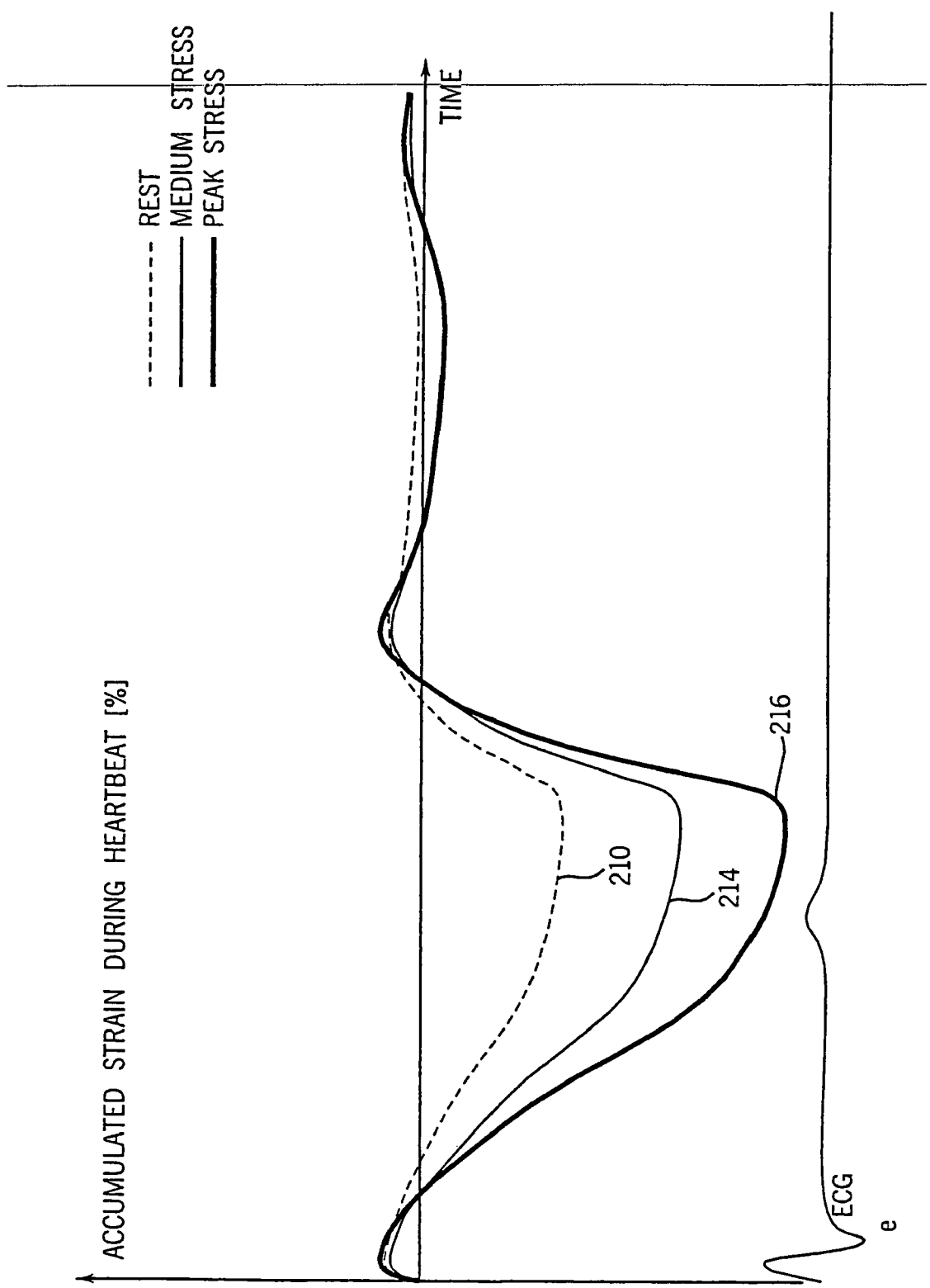
FIG. 10 illustrates a display of accumulated strain from multiple stress levels as a function of time for a normal case according to a preferred embodiment of the present invention.
Figure 11:
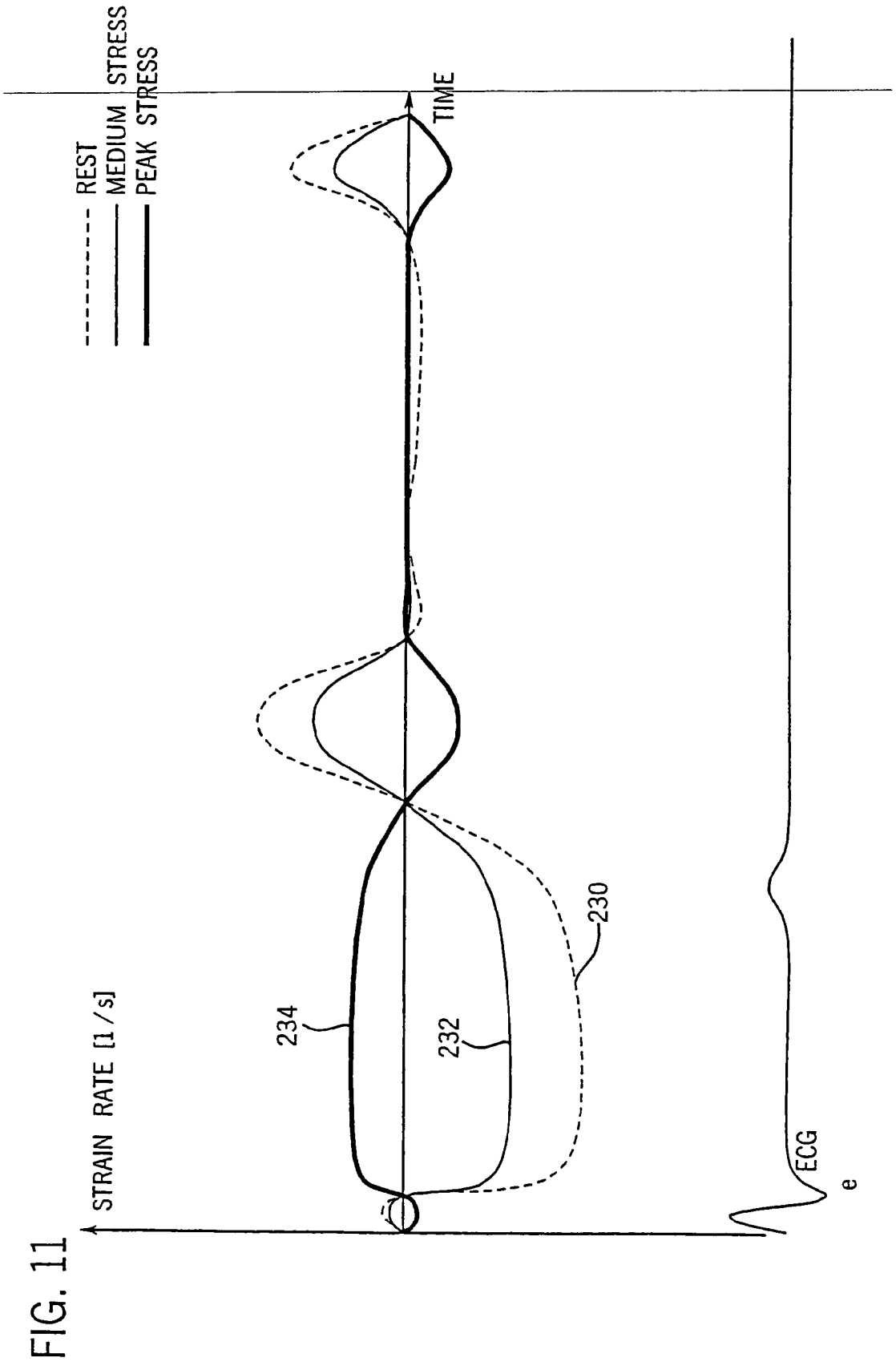
FIG. 11 illustrates a display of strain rate from multiple stress levels as a function of time for a pathological case according to a preferred embodiment of the present invention.
Figure 12:
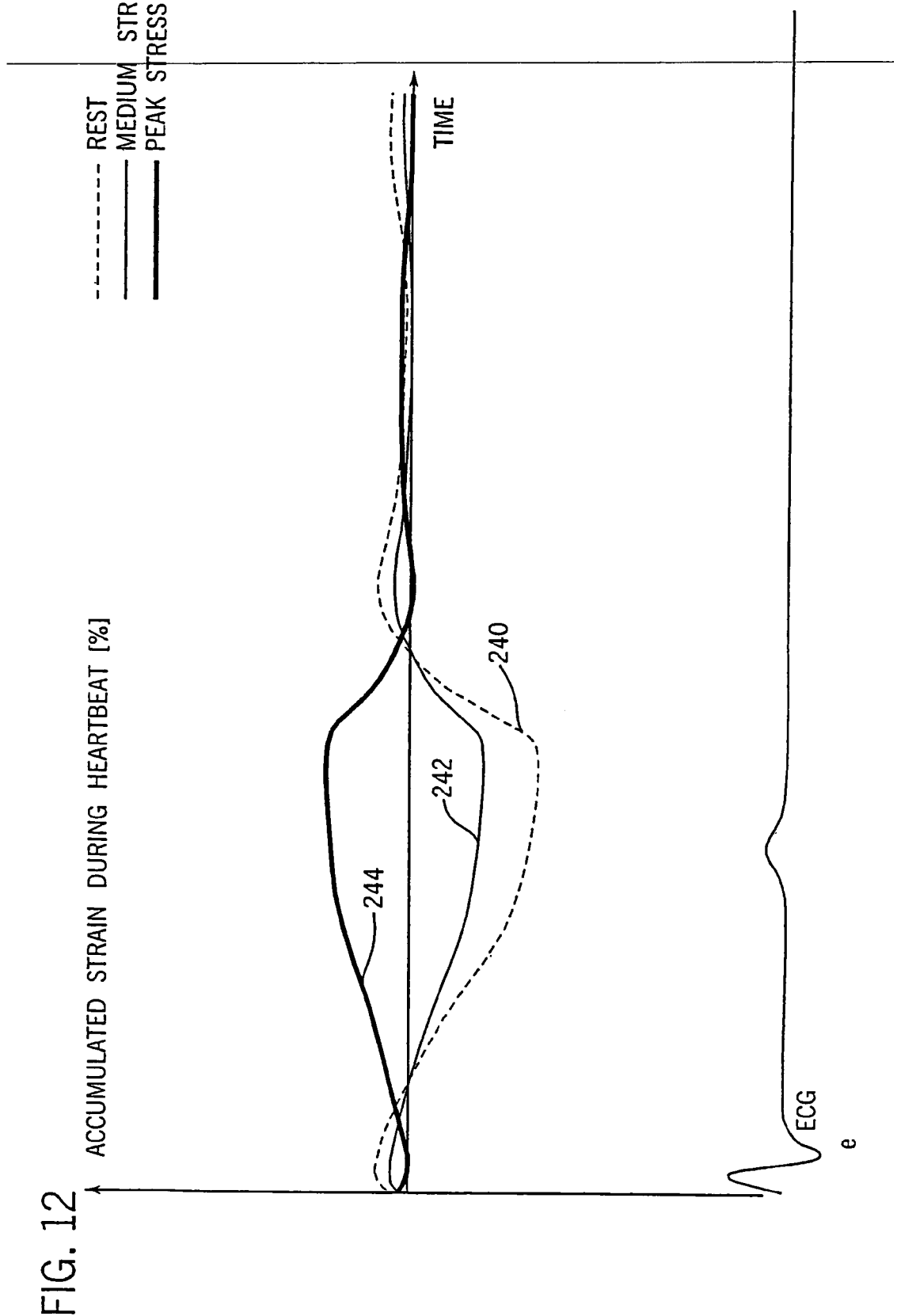
FIG. 12 illustrates a display of accumulated strain from multiple stress levels as a function of time for a pathological case according to a preferred embodiment of the present invention.

FIG. 10 is identical to FIG. 9 except that accumulated strain is plotted for rest (line 210), medium stress (line 212) and peak stress (line 214) instead of the instantaneous strain rate. The FIG. 10 demonstrates how the longitudinal shortening increases as a function of stress level. FIGS. 11 and 12 correspond to FIGS. 9 and 10, respectively, except that FIG. 11 illustrates a typical pathological reading of strain rates for rest (line 230), medium stress (line 232) and peak stress (line 234), and FIG. 12 illustrates a typical pathological reading of accumulated strain for rest (line 240), medium stress (line 242) and peak stress (line 244). The example of FIGS. 11 and 12 illustrates a case with normal rest values for longitudinal shortening, but with a reduction in shortening when the stress level increases. At peak stress the curves illustrate a reverse in both strain rate and strain which can indicate passive stretching of the local wall segment.

Figure 13:
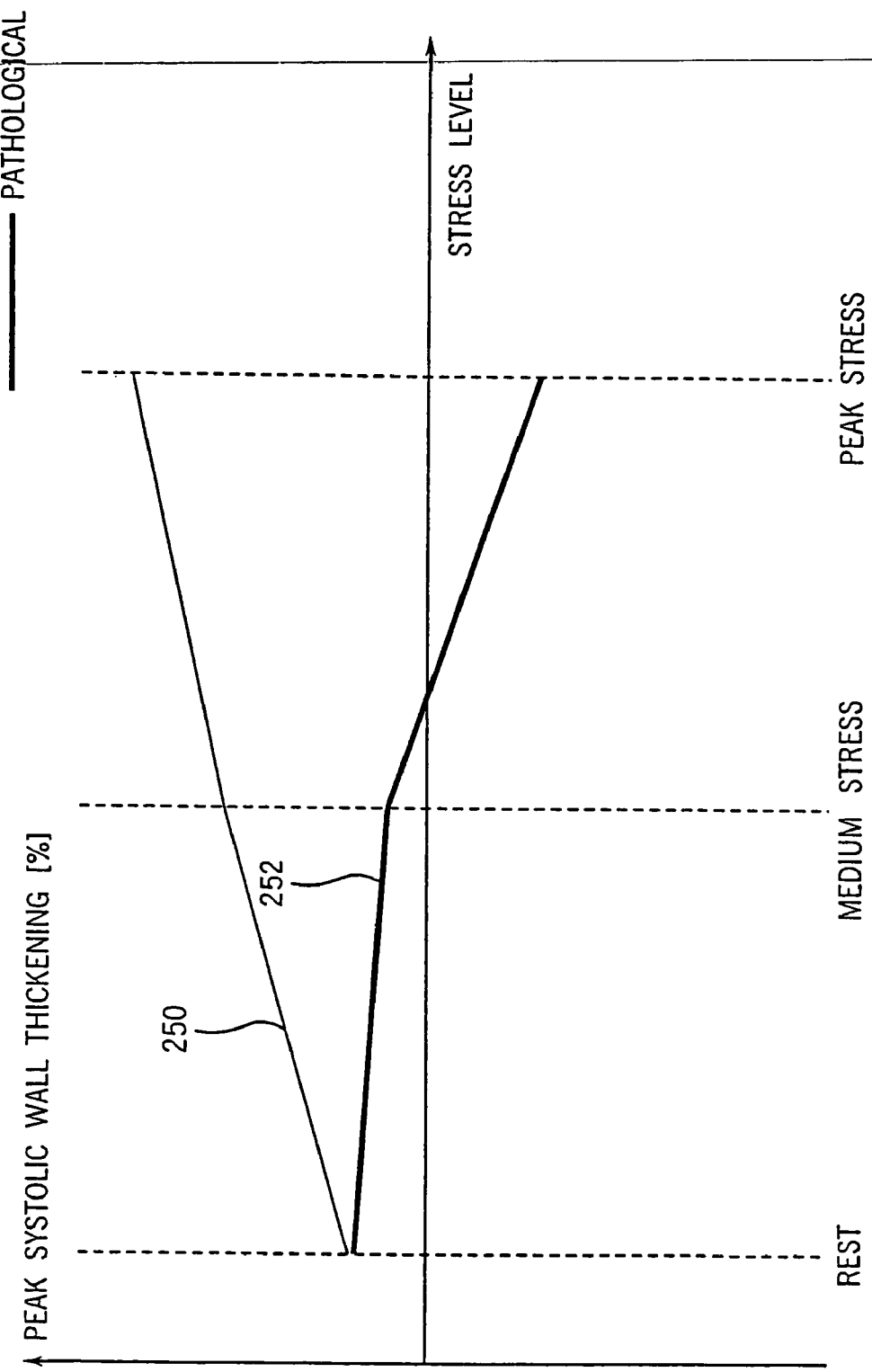
FIG. 13 illustrates a display of a strain derived parameter, peak systolic wall thickening, as a function of stress level according to a preferred embodiment of the present invention.

FIG. 13 illustrates how characteristic values extracted from the strain information for a given location or wall segment can be displayed as a function of stress level. The example in FIG. 13 is the maximal systolic longitudinal shortening which is plotted as a function of stress level. The normal case (line 250) with a uniform increase in longitudinal shortening and the pathological case (line 252) with a decrease in longitudinal shortening and even a switch to passive stretching during systole are illustrated.

Another useful way to present the quantitative parameters derived from strain is in a Bulls-eye plot by either numerically or graphically labeling each of the areas corresponding to LV segments according to the associated strain derived parameters. The values illustrated in FIG. 13 are examples of such useful strain derived parameters.

In the foregoing specification the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarding in an illustrative rather than restrictive sense.

The invention claimed is:

1. A method for generating tissue deformation information comprising:
   acquiring echo signals for a plurality of beams and a plurality of range positions along ultrasonic beams in an area of interest to cover a spatial region;
   determining a beam angle between the ultrasonic beams and a principle direction for local tissue deformation;
   computing at least one angle corrected tissue deformation parameter along said principal direction for at least one spatial location, wherein said computation of at least one angle corrected tissue deformation parameter comprises:
   (i) computing a radial velocity gradient radially along the ultrasound beam;
   (ii) computing a lateral velocity gradient laterally between beams at a fixed range location; and
   (iii) deriving angle corrected tissue deformation parameters as a linear combination of said radial and lateral velocity gradients determined by said beam angle; and
   displaying at least one of the said angle corrected tissue deformation parameters on a display unit.

2. The method according to claim 1 wherein said ultrasonic beams are generated with a high lateral resolution inside said area of interest.

3. The method according to claim 2 wherein changes in at least one of said angle corrected tissue deformation parameters is displayed as a function of time for a given anatomical location.

4. The method according to claim 2 wherein the said display is a M Mode display displaying at least one of said angle corrected tissue deformation parameters with time versus location on said user defined polygon.

5. The method according to claim 1 wherein the said beam angle determination is computed based on a direction along and perpendicular to a user defined polygon.

6. The method according to claim 1 further comprising:
   spatially averaging said radial and lateral velocity gradients.

7. A method for generating tissue deformation information comprising:
   determining a beam angle between ultrasonic beams and a principle direction for local tissue deformation;
   computing at least one angle corrected tissue deformation parameter along said principal direction for at least one spatial location by: (i) computing a radial velocity gradient radially along the ultrasound beams, (ii) computing a lateral velocity gradient laterally between beams at a fixed range location, and (iii) deriving angle corrected tissue deformation parameters as a linear combination of said radial and lateral velocity gradients determined by said beam angle; and
   displaying at least one of the said angle corrected tissue deformation parameters on a display unit.

8. The method of claim 7 further comprising spatially averaging said radial and lateral velocity gradients.

9. A method for computing at least one angle corrected tissue deformation parameter along a principal direction for at least one spatial location comprising:
   computing a radial velocity gradient radially along an ultrasound beam;
   computing a lateral velocity gradient laterally between a plurality of ultrasound beams at a fixed range location; and
   deriving angle corrected tissue deformation parameters as a linear combination of said radial and lateral velocity gradients determined by a beam angle.

10. The method according to claim 9 further comprising spatially averaging said radial and lateral velocity gradients.

11. The method according to claim 9 further comprising displaying at least one of the angle corrected tissue deformation parameters on a display unit.

12. The method according to claim 11 wherein the ultrasonic beams are generated with a high lateral resolution inside an area of interest.

13. The method according to claim 11 wherein beam angle determination is computed based on a direction along and perpendicular to a user defined polygon.

14. The method according to claim 13 wherein the display is a M Mode display displaying at least one of the angle corrected tissue deformation parameters with time versus location on said user defined polygon.

15. The method according to claim 11 wherein changes in at least one of the angle corrected tissue deformation parameters is displayed as a function of time for a given anatomical location.

* * * * *